United States Patent
Matsumoto et al.

(10) Patent No.: US 10,458,959 B2
(45) Date of Patent: Oct. 29, 2019

(54) METHOD OF DETECTING FAILURE OR ANOMALY OF SENSOR TERMINAL

(71) Applicant: Hitachi, Ltd., Tokyo (JP)

(72) Inventors: Hisanori Matsumoto, Tokyo (JP); Shiro Mazawa, Tokyo (JP); Michio Iguchi, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 352 days.

(21) Appl. No.: 15/518,896

(22) PCT Filed: Mar. 23, 2015

(86) PCT No.: PCT/JP2015/058654
§ 371 (c)(1),
(2) Date: Apr. 13, 2017

(87) PCT Pub. No.: WO2016/151716
PCT Pub. Date: Sep. 29, 2016

(65) Prior Publication Data
US 2017/0241958 A1    Aug. 24, 2017

(51) Int. Cl.
*G01N 29/30*   (2006.01)
*G01H 1/00*    (2006.01)
*G01H 3/00*    (2006.01)

(52) U.S. Cl.
CPC ............. *G01N 29/30* (2013.01); *G01H 1/00* (2013.01); *G01H 3/005* (2013.01)

(58) Field of Classification Search
CPC ............. G01N 29/30; G01N 29/14; G01N 2291/0422; G01N 29/12; G01N 29/348;
(Continued)

(56) References Cited

U.S. PATENT DOCUMENTS

2003/0033878 A1* 2/2003 Dubois ............ G01N 29/0645
73/600
2003/0117893 A1   6/2003 Bary
(Continued)

FOREIGN PATENT DOCUMENTS

JP   62-228920 A   10/1987
JP   10-026669 A    1/1998
(Continued)

OTHER PUBLICATIONS

English Translation, Hiuga Tatsuo, Abnormality discriminating method for sensor, Oct. 1987 (Year: 1987).*
(Continued)

*Primary Examiner* — John Fitzgerald
*Assistant Examiner* — Truong D Phan
(74) *Attorney, Agent, or Firm* — Mattingly & Malur, PC

(57) ABSTRACT

There is disclosed a method of detecting failures or anomalies of a large number of sensor terminals without using manpower or expensive equipment in the seismic exploration business. The method includes preparing a plurality of sensor terminals having sensors that detect vibrations from outside, the plurality of sensor terminals receiving the vibrations and outputting vibration reception signals, and comparing a first vibration reception signal output by a first sensor terminal with a second vibration reception signal output by a second sensor terminal, thereby detecting if one of the first sensor and the second sensor is failed or anomalous.

5 Claims, 17 Drawing Sheets

(58) Field of Classification Search
CPC ... G01N 2291/2634; G01N 2291/2696; G01H 3/005; G01H 1/00; G01H 13/00; G01H 1/003; G01S 7/5205; G01M 3/243; G01M 13/045
USPC .......................... 73/1.82, 587, 579, 592, 593
See application file for complete search history.

(56) References Cited

U.S. PATENT DOCUMENTS

| | | | |
|---|---|---|---|
| 2005/0210954 A1* | 9/2005 | Raffalt | G01F 23/2967 73/1.82 |
| 2011/0230304 A1* | 9/2011 | Morel | B64C 27/12 475/331 |
| 2017/0067859 A1* | 3/2017 | Kolb | G01N 29/30 |
| 2017/0344935 A1* | 11/2017 | Mattingly | G06K 7/10366 |

FOREIGN PATENT DOCUMENTS

| | | |
|---|---|---|
| JP | 2000-045569 A | 2/2000 |
| JP | 2003-232865 A | 8/2003 |

OTHER PUBLICATIONS

English Translation, Ganmi Tatsuya, Vibration damping device, Feb. 2000 (Year: 2000).*
International Search Report of PCT/JP2015/058654 dated Jun. 23, 2015.

* cited by examiner

METHOD OF DETECTING FAILURE OR ANOMALY OF SENSOR TERMINAL

TECHNICAL FIELD

The present technology relates to a method for detecting the failure or anomaly of a sensor terminal used for physical exploration, and in particular, relates to a method for detecting the failure or anomaly of a sensor terminal used for seismic exploration, in which seismic exploration is performed especially for exploring oil resources including all kinds of mineral hydrocarbons, that is, solid, liquid, and gaseous mineral hydrocarbons.

BACKGROUND ART

The exploration business of oil resources needs a huge amount of money, and at the same time, it is a very risky business. As a trend in the oil industry, the expansion of the exploration fields of oil resources and the tremendous increase in the number of sensor terminals have been extensively pursued in order to reduce the cost and increase the accuracy of the exploration of oil resources. Here, the sensor terminals refer to sensor terminals capable of detecting vibrations such as geophones, semiconductor sensors, and MEMS sensors that are used mainly for seismic exploration. A next generation system for seismic exploration sets it as its goal to implement one million sensor terminals per system, and therefore, in order to achieve this goal, it becomes necessary to perform such operations as burying thirty thousand sensor terminals in fields per day; retrieving thirty thousand sensor terminals per day; acquiring data from thirty thousand sensor terminals per day; and maintaining thirty thousand sensor terminals per day. Therefore, to make a seismic exploration business flow more efficient becomes a very important factor for determining the cost of the exploration work.

For example, Patent Literature 1 discloses a system in which a relay apparatus for collecting seismic data is made to have a function for testing and checking the capabilities of terminals in order to make the seismic exploration business more efficient.

CITATION LIST

Patent Literature

Patent Literature 1: Japanese Unexamined Patent Application Publication No. 2003-232865

SUMMARY OF INVENTION

Technical Problem

Among seismic exploration work, the work of collecting data from a large number of terminals retrieved every day and the work of maintaining those terminals are most time-consuming and laborious work. The maintenance work includes the work of charging sensor terminals and the work of detecting the failures or anomalies of sensor terminals, and especially there has been no effective method for detecting failures or anomalies so far. Here, a failure refers to a state of a sensor terminal in which a sensor terminal outputs a vibration reception signal unrelated with a vibration applied to the sensor from outside, and for example, such a state includes a state in which the vibration reception signal is a random signal, or a constant signal (including a signal with its output zero).

On the other hand, an anomaly refers to a state in which the difference between the actual value of a vibration applied to a sensor terminal and a value recorded as a vibration reception signal exceeds an acceptable value, and this acceptable value of the difference is determined in accordance with an analysis accuracy needed by seismic exploration performed by each project of an oil development business.

In the seismic exploration business industry, a method for detecting the failures and anomalies of a large number of sensor terminals without using manpower or expensive equipment is strongly desired.

Solution to Problem

A method disclosed by the present invention includes: preparing a plurality of sensor terminals having sensors that detect vibrations from outside, the plurality of sensor terminals receiving the vibrations and outputting vibration reception signals; and comparing a first vibration reception signal output from a first sensor terminal with a second vibration reception signal output from a second sensor terminal, thereby detecting if one of the sensors is failed or anomalous.

Another method disclosed by the present invention includes: preparing a plurality of sensor terminals having sensors that detect vibrations from outside, the plurality of sensor terminals receiving the vibrations and outputting vibration reception signals; and comparing a first vibration reception signal output from a first sensor terminal with a second vibration reception signal output from a second sensor terminal, thereby detecting if one of the sensors is failed or anomalous, in which the plurality sensor terminals are housed in slots arranged in the shape of a lattice, and the first sensor terminal and the second sensor terminal are selected from among sensor terminals housed in slots located adjacently. Here, the shape of a lattice refers to the shape of a grid lattice, the shape of a triangular lattice, the shape of a hexagonal lattice, or the like.

Advantageous Effects of Invention

The present invention does not require a reference sensor for detecting the failure or anomaly of a sensor, hence the cost of the apparatus for detecting the failure or anomaly of a sensor can be reduced. In addition, because processes for detecting the failure or anomaly can be automated, manpower costs can be reduced.

DESCRIPTION OF EMBODIMENTS

First Embodiment

In this embodiment, fundamental examples of an apparatus configuration and a processing flow for realizing a detection method according to the present invention will be shown.

Figure 1:
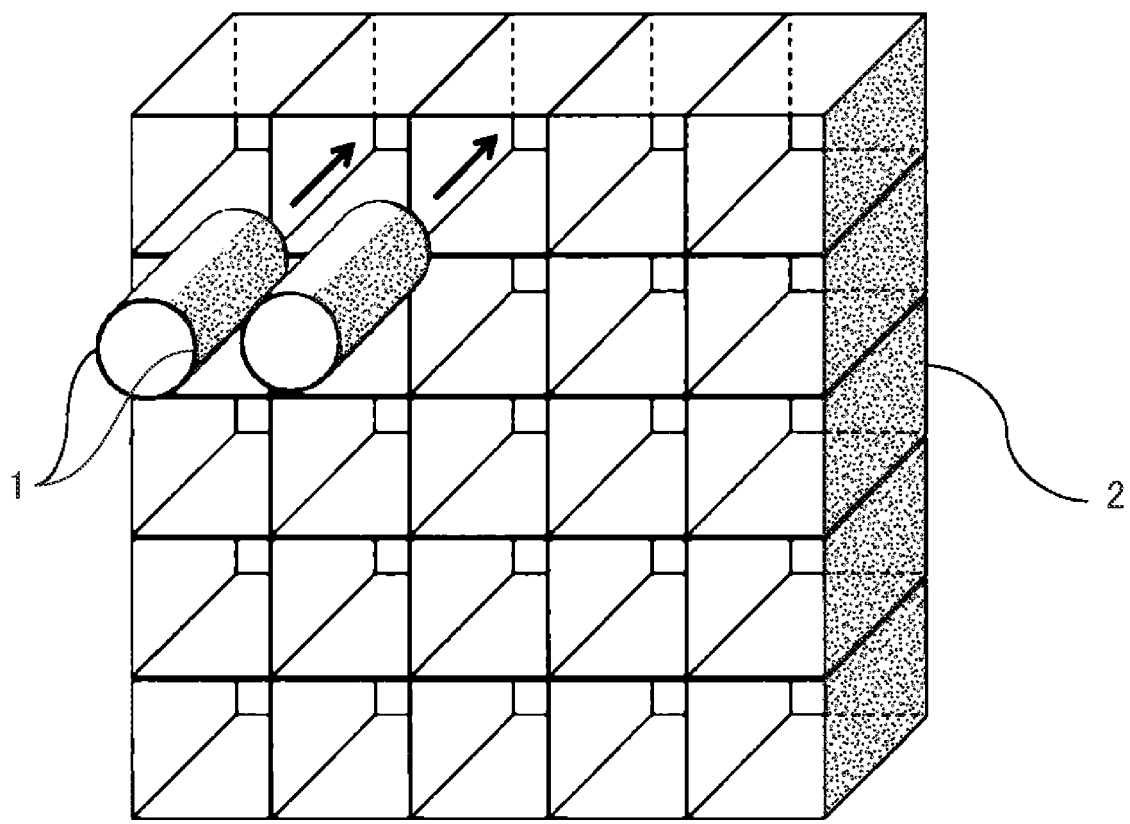
FIG. 1 is the schematic diagram of the apparatus configuration of a first embodiment that can be used for a detection method according to the present invention.

FIG. 1 is the schematic diagram of an apparatus configuration that can be used for a detection method according to the present invention. A housing device 2 includes slots of the shape of a grid lattice for housing plural sensor terminals 1. Each slot has means for detecting whether a sensor terminal 1 is housed in itself or not, and the housing device 2 can always grasp in which slots sensor terminals 1 are housed. The means for detecting whether a sensor terminal 1 is housed in a slot or not can be realized with the use of, for example, a mechanical switch, an RFID, local wireless communication means, an infrared sensor, an image sensor. When the housing device 2 detects that a sensor terminal 1 is housed in a certain slot, the housing device 2 establishes communication connection with the sensor terminal 1, and receives a vibration reception signal output by the sensor terminal 1.

From among vibration reception signals output from the plural sensor terminals 1 housed in the housing device 2, for example, a first vibration reception signal output from a first sensor terminal 1 and a second vibration reception signal output from a second sensor terminal 2 are compared, and it is judged if one of the first sensor terminal 1 and the second sensor terminal 1 is failed or anomalous. In other words, as a result of comparing the first vibration reception signal and the second vibration reception signal, if their values agree with each other, it can be judged that both first sensor terminal 1 and the second sensor terminal 1 are normal.

On the other hand, if the values of the first vibration reception signal and the second vibration reception signal do not agree with each other, it can be judged that one of the first sensor terminal 1 and the second sensor terminal 1 is failed or anomalous. In this case, it is assumed that a probability that a sensor terminal 1 is normal is sufficiently larger than a probability that the sensor terminal 1 is failed or anomalous.

Figure 16:
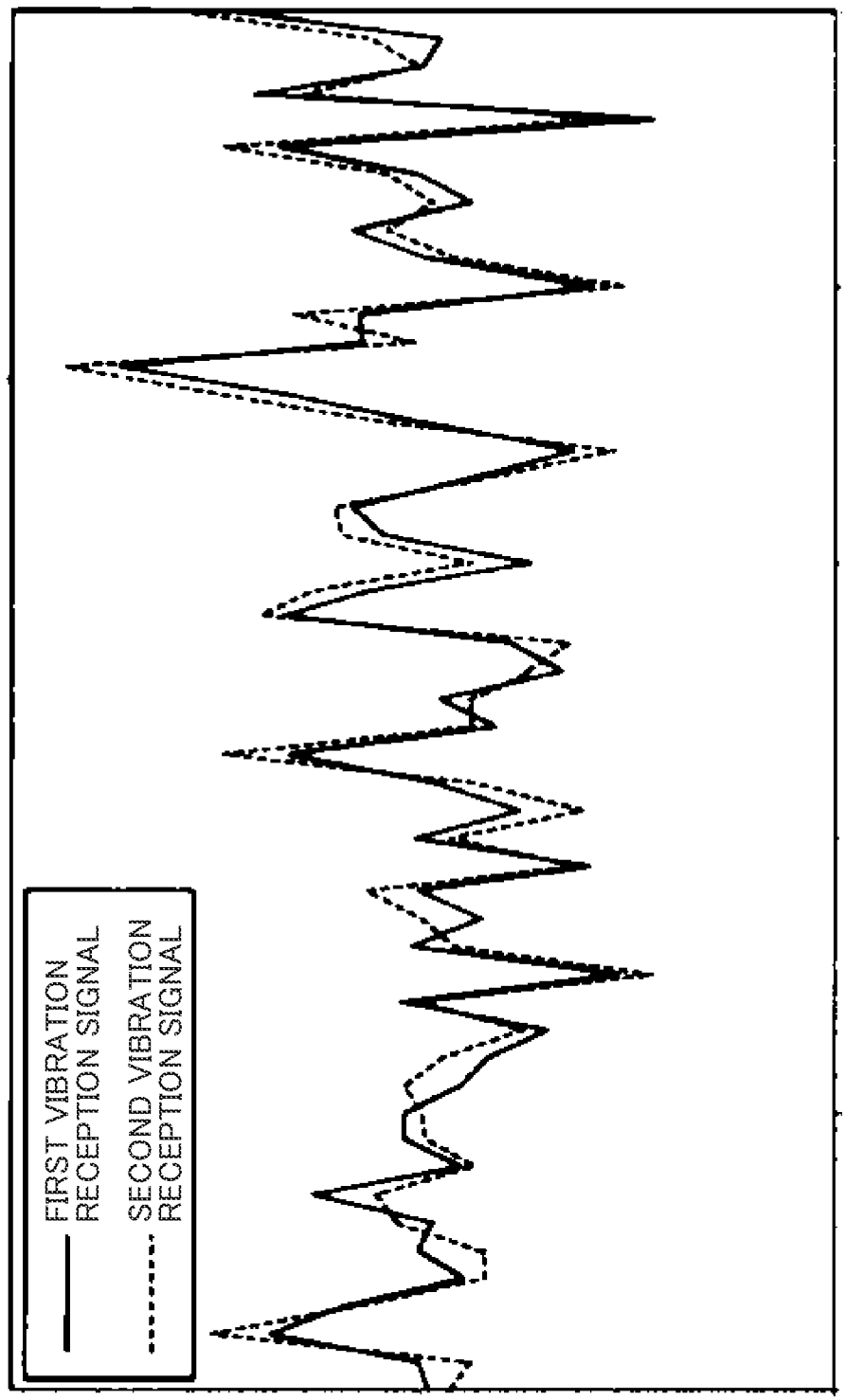
FIG. 16 shows a first vibration reception signal and a second vibration reception signal.

The judgment whether the values of the first vibration reception signal and the second vibration reception signal agree with each other or not is quantitatively executed using an index based on probability statistics. As an example, a method in which the judgment is executed using a correlation coefficient will be explained with reference to FIG. 16. FIG. 16 shows an example of the first vibration reception signal received from the first sensor terminal 1 and an example of the second vibration reception signal received from the second sensor terminal 2. As shown in FIG. 16, because each of the first vibration reception signal 1 and the second vibration reception signal includes an error, the first vibration reception signal 1 and the second vibration reception signal do not completely agree with each other. In order to estimate the degree of agreement between the first vibration reception signal and the second vibration reception signal, the correlation coefficient between these two signals is calculated using the following Expression 1.

[Expression 1]

$$C = \frac{\sum_{i=1}^{N}(x_i - X)(y_i - Y)}{\sqrt{\left[\sum_{i=1}^{N}(x_i - X)^2\right]\left[\sum_{i=1}^{N}(y_i - Y)^2\right]}} \quad \text{(Expression 1)}$$

In Expression 1, C is a correlation coefficient, $x_i$ is the ith sampling value of the first vibration reception signal, X is the average value of the first vibration reception signal, $y_i$ is the ith sampling value of the second vibration reception signal, Y is the average value of the second vibration reception signal, and N is the sampling number of the first vibration reception signal and it is also the sampling number of the second vibration reception signal. By setting the value of the correlation coefficient calculated using Expression 1 as a threshold, the judgment of agreement or disagreement can be made using this threshold. For example, if 0.8 is set to the threshold, when the value of the correlation coefficient is equal to 0.8 or larger, it is judged that the first vibration reception signal and the second vibration reception signal agree with each other, and when the value of the correlation coefficient smaller than 0.8, it is judged that the first vibration reception signal and the second vibration reception signal do not agree. Furthermore, the value of the threshold is determined in accordance with an accuracy and the like needed by a data analysis executed in an after-mentioned process. Here, a correlation coefficient between the first vibration reception signal and the second vibration reception signal shown in FIG. 16 calculated using Expression 1 is about 0.934.

Alternatively, the quantitative reference numerical value used for the judgment of agreement or disagreement can be a variance, an error of mean square, a residual error, or the like instead of a correlation coefficient.

Vibrations from outside that a sensor terminal 1 detects in this detection method according to the present invention can be vibrations generated by a vibration exciting device, or can be natural vibrations generated by ambient surroundings. If natural vibrations are used as vibrations from outside, a vibration exciting device becomes unnecessary, therefore the cost of the housing device can be lowered further.

Figure 2:
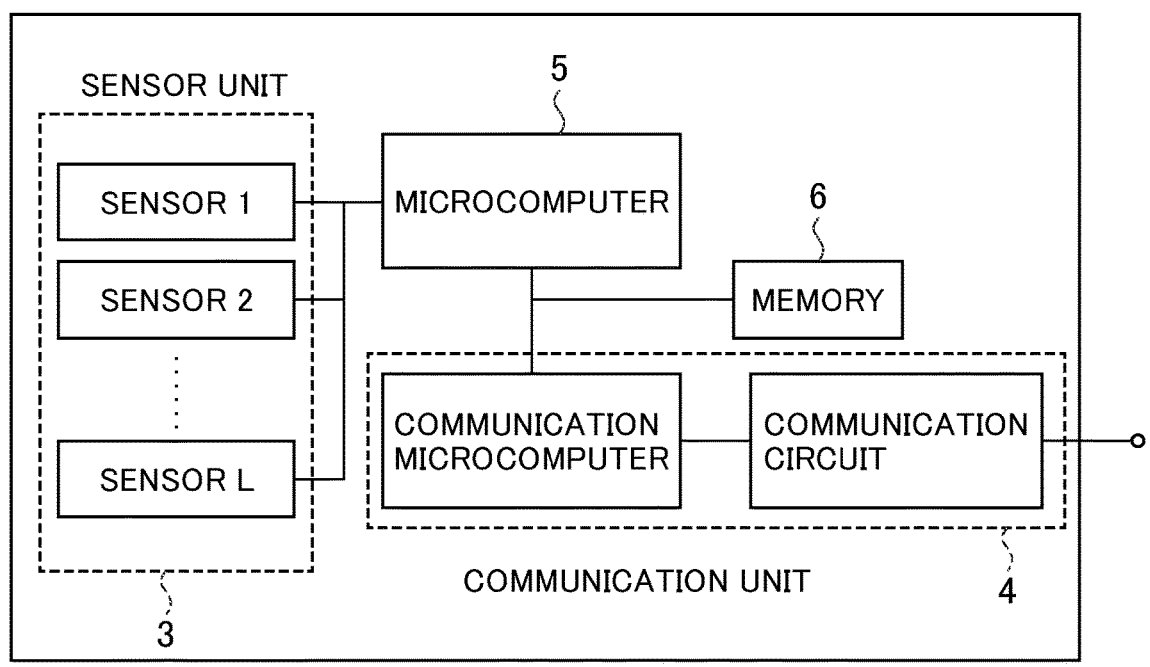
FIG. 2 is a block diagram of a sensor terminal of the first embodiment.

FIG. 2 is a block diagram showing the internal configuration of a sensor terminal 1. The sensor terminal 1 includes: a sensor unit 3 including a sensor 1 to a sensor L; a communication unit 4 including a communication microcomputer and a communication circuit; a microcomputer 5; and a memory 6. The sensor 1 to the sensor L that are included in the sensor unit 3 are, for example, acceleration sensors; velocity sensors; GNSS vibration reception devices; temperature sensors; illumination sensors; humidity sensors; or pressure sensors, and the sensor 1 to the sensor L include at least one sensor. It is preferred that the communication unit 4 should perform wireless communication with a communication circuit 8 of the housing device 2, and should be capable of utilizing, for example, a wireless LAN compliant with IEEE 802.11a, b, g, n, or the like, or a wireless PAN system compliant with Bluetooth (registered trademark), transferjet, UWB or the like. In the case where a wireless communication system is adopted in the communication unit 4, an antenna, a coupler, or the like is connected to the terminal of the communication unit 4. Alternatively, a wire communication system can be adopted to realize the communication unit 4, and in this case, a connector with metal contacts is connected to the connection terminal of the communication unit 4.

The microcomputer 5 performs the control of the sensor 1 to sensor L included in the sensor unit 3, and data output from the sensor 1 to sensor L is stored in the memory 6. In this case, the control of the sensor 1 to sensor L includes turning the power supply of each sensor on and off, switching between operation modes (a measurement mode, a sleep mode, a standby mode, and the like) of each sensor, switching between the ranges of the sensing sensitivity of each sensor, and the like.

Figure 3:
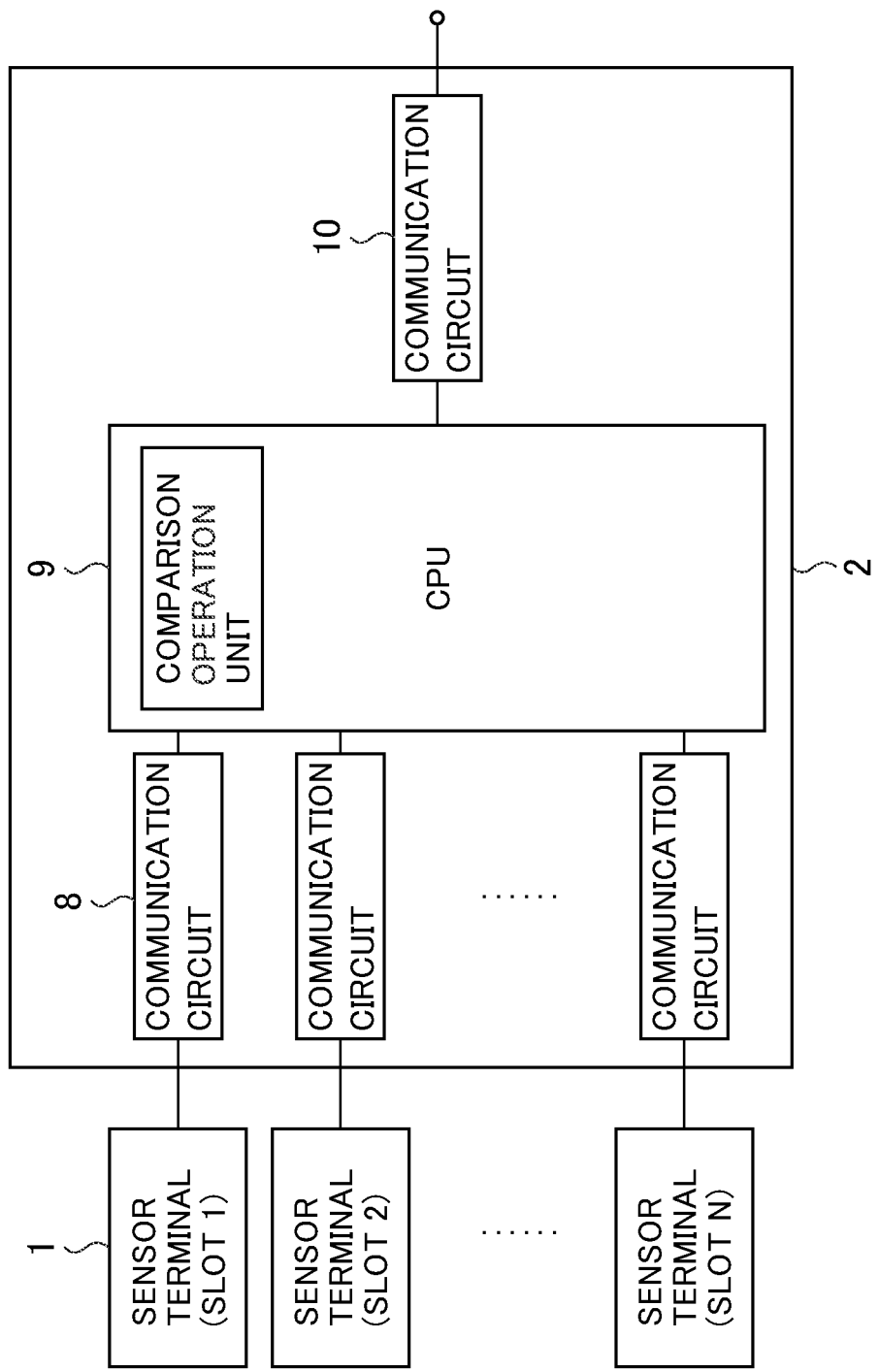
FIG. 3 is a block diagram of the apparatus configuration of the first embodiment.

FIG. 3 is a block diagram of the apparatus configuration that can be used for a detection method according to the present invention. N sensor terminals 1 (wherein N represents the number of sensor terminals 1) are housed in the slot 1 to slot N of the housing device 2 one-on-one (wherein the slot 1 to the slot N are slots each of which houses a sensor terminal 1 and is disposed at arbitrary coordinates). The housing device 2 includes plural communication circuits 8 for connecting to the sensor terminals 1, a CPU 9, and a communication circuit 10 for connecting to upper external devices. The housing unit 2 detects that a sensor terminal 1 is mounted in each slot with the use of means (not shown in FIG. 3) for detecting that a sensor terminal 1 is housed or not, establishes connection to the sensor terminal 1 via a communication circuit 8, and receives a vibration reception signal. A comparison operation unit is installed programmatically in the CPU 9, and the CPU 9 executes a comparison procedure on vibration reception signals. The communication circuit 10 can transfer vibration reception signals or the result of the comparison procedure to an upper server, a storage, and the like.

The RF circuit unit and the baseband circuit unit of a wireless LAN compliant with IEEE802.11a, b, g, or n or the like, or the RF circuit unit and the baseband circuit unit of a wireless PAN system compliant with Bluetooth, transferjet, UWB, or the like are implemented in a communication circuit 4. Electric signals output by the sensor 1 to the sensor L included in the sensor unit 3 having the sensor terminals 1 are transmitted to the CPU 9 via the communication circuit 4.

Figure 4:
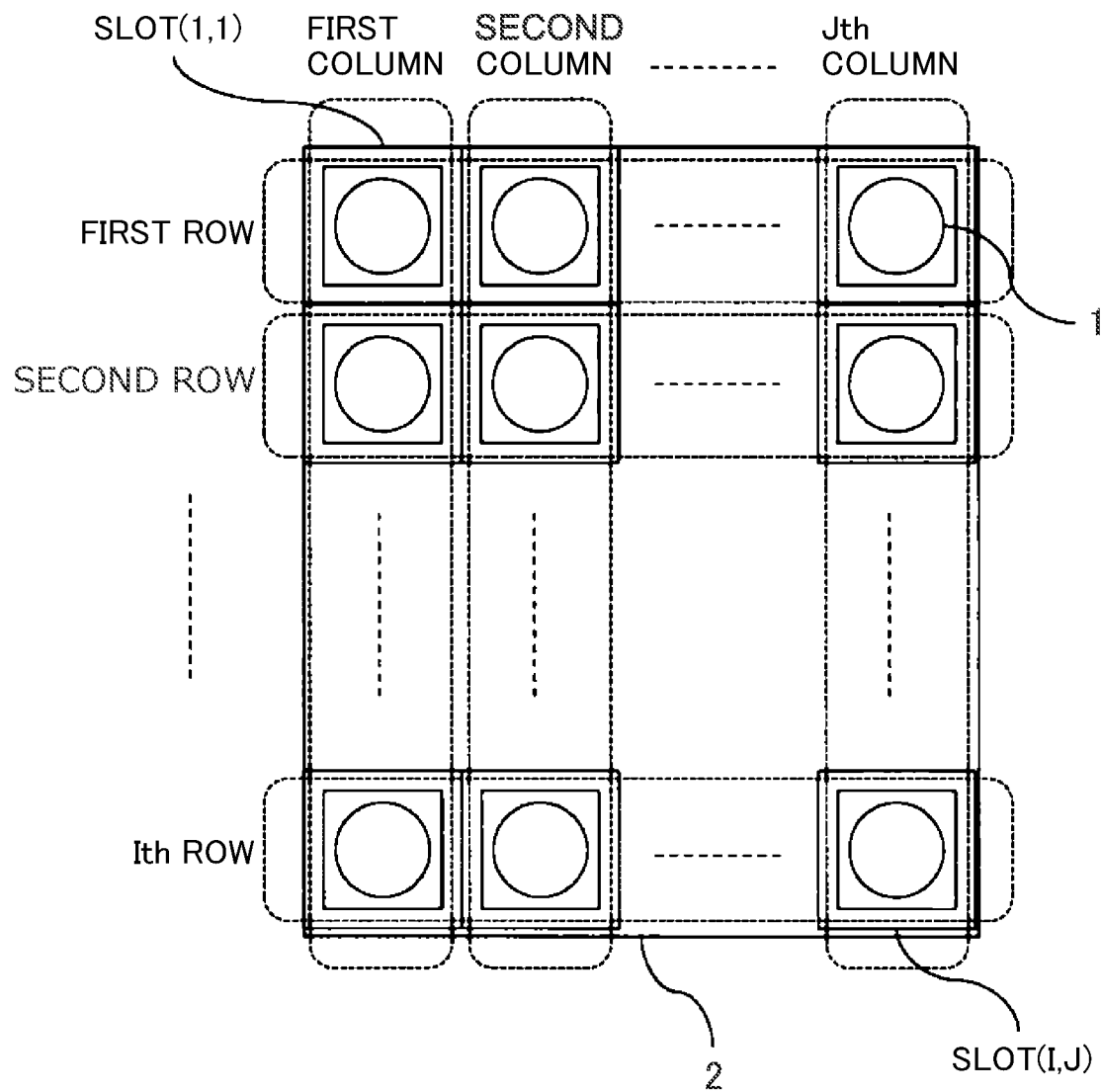
FIG. 4 is a diagram showing the slot arrangement of a housing device of the first embodiment.
Figure 17:
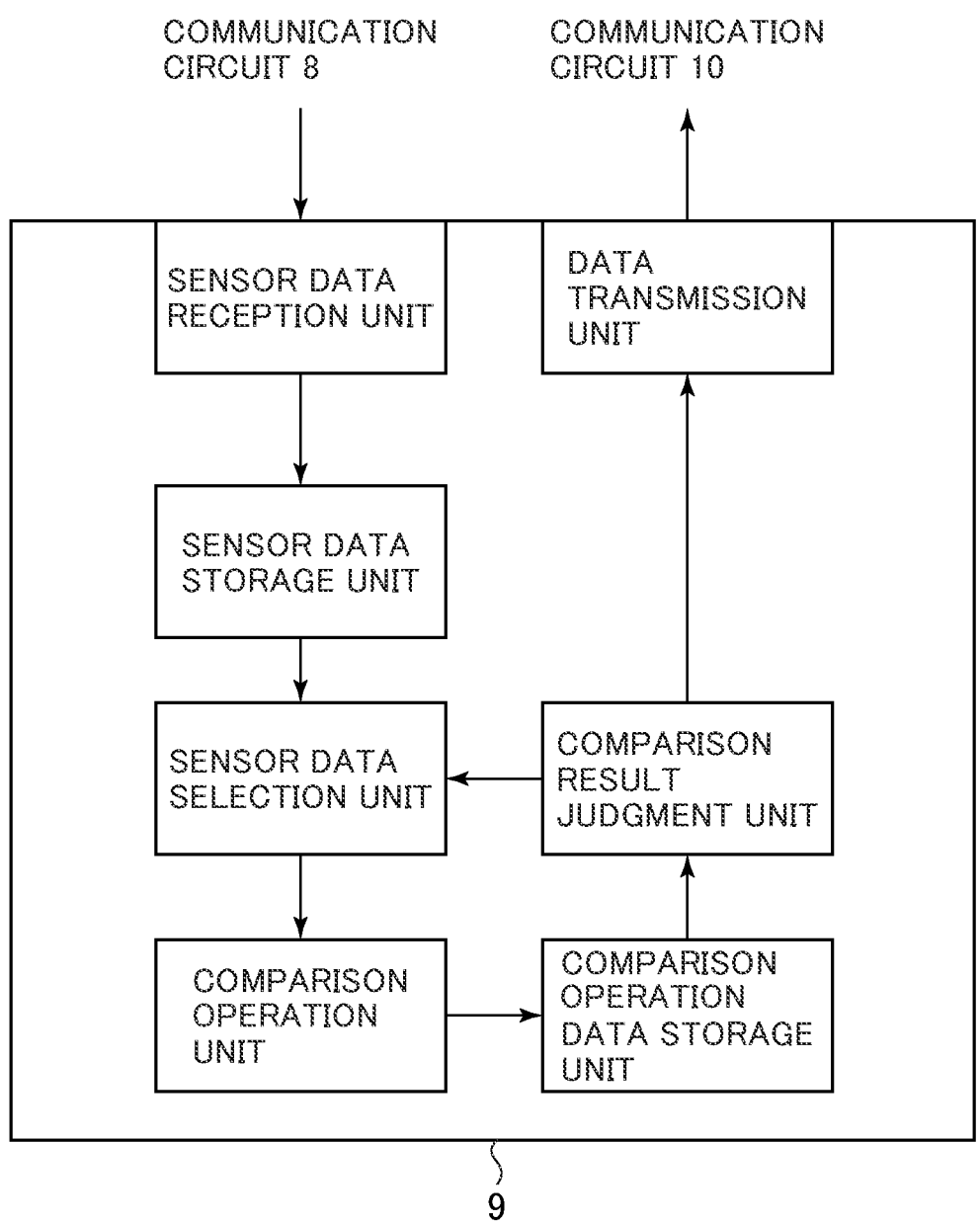
FIG. 17 is a block diagram of internal processing executed by a CPU.

FIG. 17 shows an example of a block configuration of internal processing executed by the CPU 9. Sensor data is stored in a sensor data storage unit via a sensor data reception unit. At least two data sets are read out from among sensor data stored in the sensor data storage unit by a sensor data selection unit, and the at least two data sets are transferred to the comparison operation unit, and a comparison operation is executed on the at least two data sets by the comparison operation unit. The result of the comparison operation output from the comparison operation unit is stored in a comparison operation data storage unit, and then the agreement or disagreement between the at least two data sets is judged by a comparison result judgment unit with reference to a specific threshold. The judgment result is transmitted to the communication circuit 10 via a data transmission unit, and is stored in an upper database and the like. Furthermore, if the comparison result judgment unit judges that the at least two data sets do not agree with each other, the sensor data selection unit is informed of this result, and the data sets that are judged not to agree with each other are compared with other data sets in order to specify which data set is anomalous. FIG. 4 is a diagram showing the slot arrangement of the housing device. The slots are arranged in the shape of a grid lattice, and a slot is represented by a slot (i, j) using coordinates (i, j), where i and j are arbitrary integers. This slot arrangement represents the arrangement of slots each of which houses a sensor terminal 1 as shown in the schematic diagram of FIG. 1, and the slots are represented in such a way that a slot (1, 1) is a slot disposed at the uppermost left of FIG. 4 and a slot (I, J) is a slot disposed at the lowermost right of FIG. 4.

Figure 5:
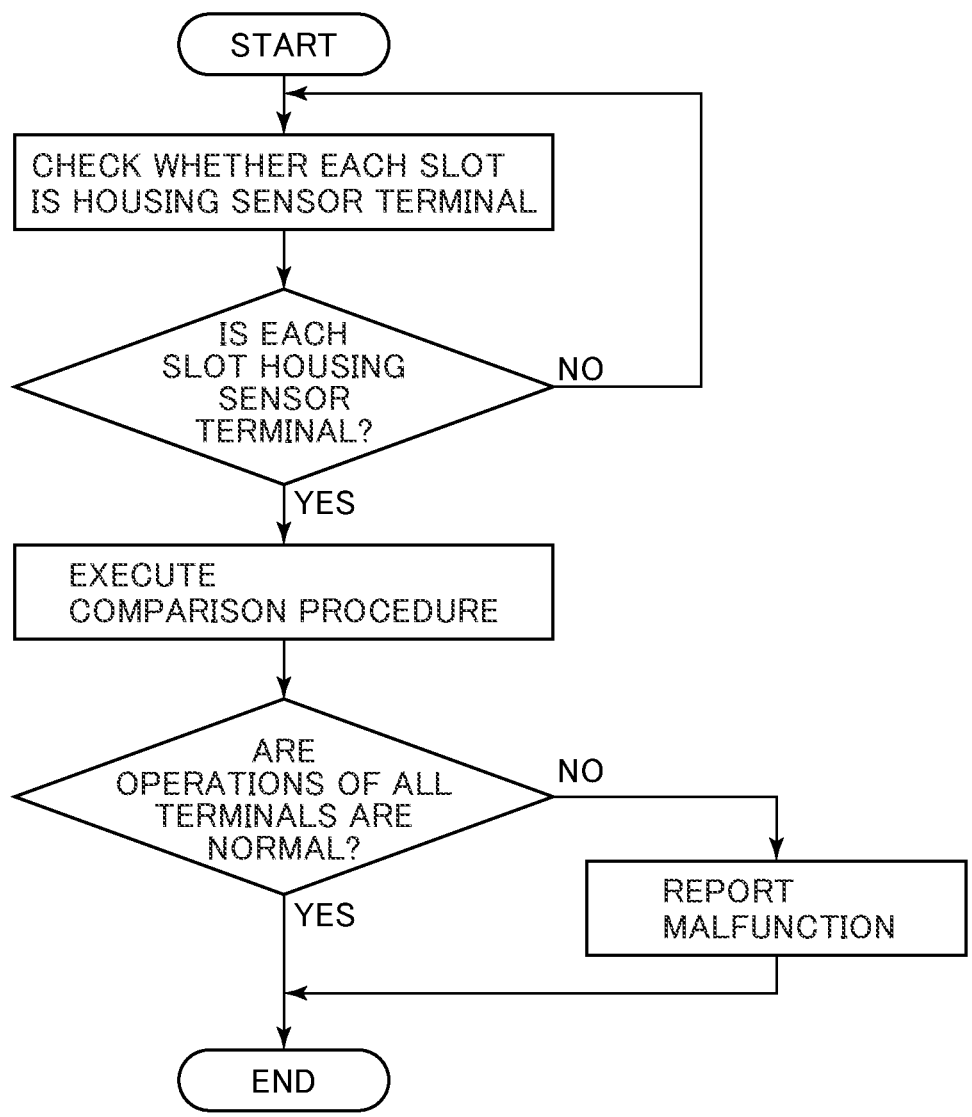
FIG. 5 is a processing flow diagram in the apparatus configuration of the first embodiment.

FIG. 5 is a processing flow diagram in the apparatus configuration. First, whether each slot is housing a sensor terminal 1 or not is checked by the housing device 2. Next, after it is detected that each slot is housing a sensor terminal 1, a comparison procedure is executed. Subsequently, as a result of the comparison procedure, if it is judged that the operations of all the terminals 1 are normal, this processing is finished. On the other hand, if the operation of any sensor terminal is failed or anomalous, this malfunction id reported to the upper server and the like, and this processing is finished.

Figure 6:
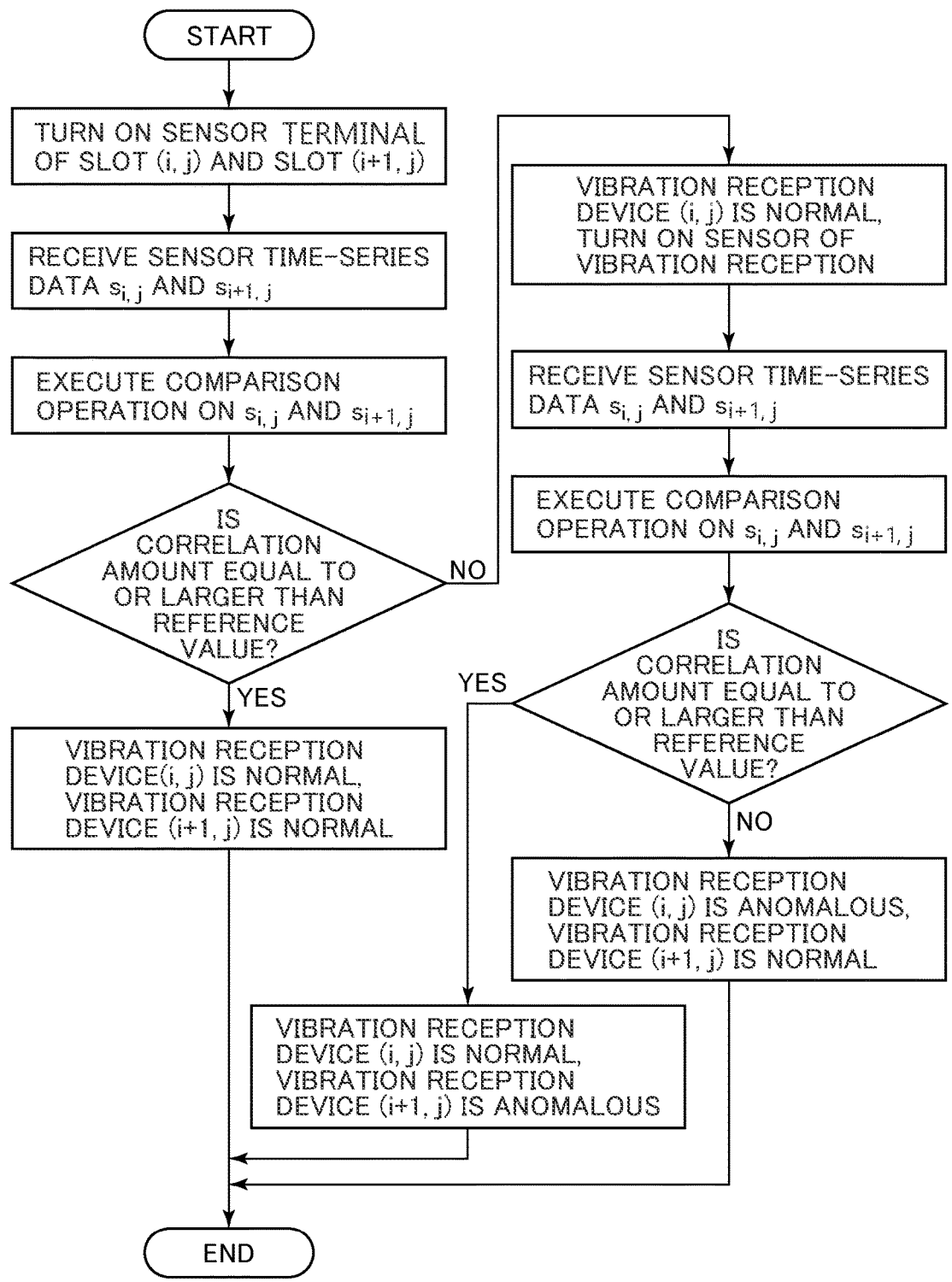
FIG. 6 is the processing flow diagram of a comparison procedure in the apparatus configuration of the first embodiment.

FIG. 6 is a processing flow diagram of the comparison procedure in the apparatus configuration. First, the housing device 2 turns on the power supplies of sensor terminals 1 of a slot (i, j) and a slot (i+1, j). Next, the housing device 2 receives time-series data $s_{i,j}$ and $s_{i+j,j}$ of the sensor terminals 1 housed respectively in the slot, j) and the slot (i+1, j). Next, a comparison operation is executed on the time-series data $s_{i,j}$ and $s_{i+1,j}$. As a result of the comparison operation, if the correlation value is equal to or larger than a reference value, it is judged that both sensor terminals 1 housed in the slot (i, j) and the slot (i+1, j) are normal, and the comparison procedure is finished. On the other hand, if the correlation value is smaller than the reference value, the housing device 2 turns on the power supply of sensor terminals 1 of the slot (i, j) and the power supply of a slot (i, j+1). Next, the housing device 2 receives time-series data $s_{i,j}$ and $s_{i,j+1}$ of the sensor terminals 1 housed respectively in the slot (i, j) and the slot (i, j+1). Next, a comparison operation is executed on the time-series data $s_{i,j}$ and $s_{i,j+1}$. As a result of the comparison operation, if the correlation value is equal to or larger than the reference value, it is judged that the sensor terminal 1 housed in the slot (i, j) is normal, and the sensor terminal 1 in the slot (i+1, j) is failed or anomalous, and the comparison procedure is finished. On the other hand, if the correlation value is smaller than the reference value, it is judged that the sensor terminal 1 housed in the slot (i, j) is failed or anomalous, and the slot (i+1, j) is normal, and the comparison procedure is finished.

The comparison operation shown in FIG. 6 is, for example, the calculation of the correlation coefficient shown by Expression 1. In addition, a judgment whether a correlation amount is equal to or larger than the reference value or not is made in such a way that, a threshold is set for a correlation coefficient for example, and if the correlation coefficient is equal to or larger than the threshold, it is judged that the relevant sensor terminal 1 is normal, and if the correlation coefficient is smaller than the threshold, it is judged that the relevant sensor terminal 1 is anomalous.

Second Embodiment

In this embodiment, another example of an apparatus configuration and another example of a processing flow for realizing a detection method according to the present invention will be explained.

Figure 7:
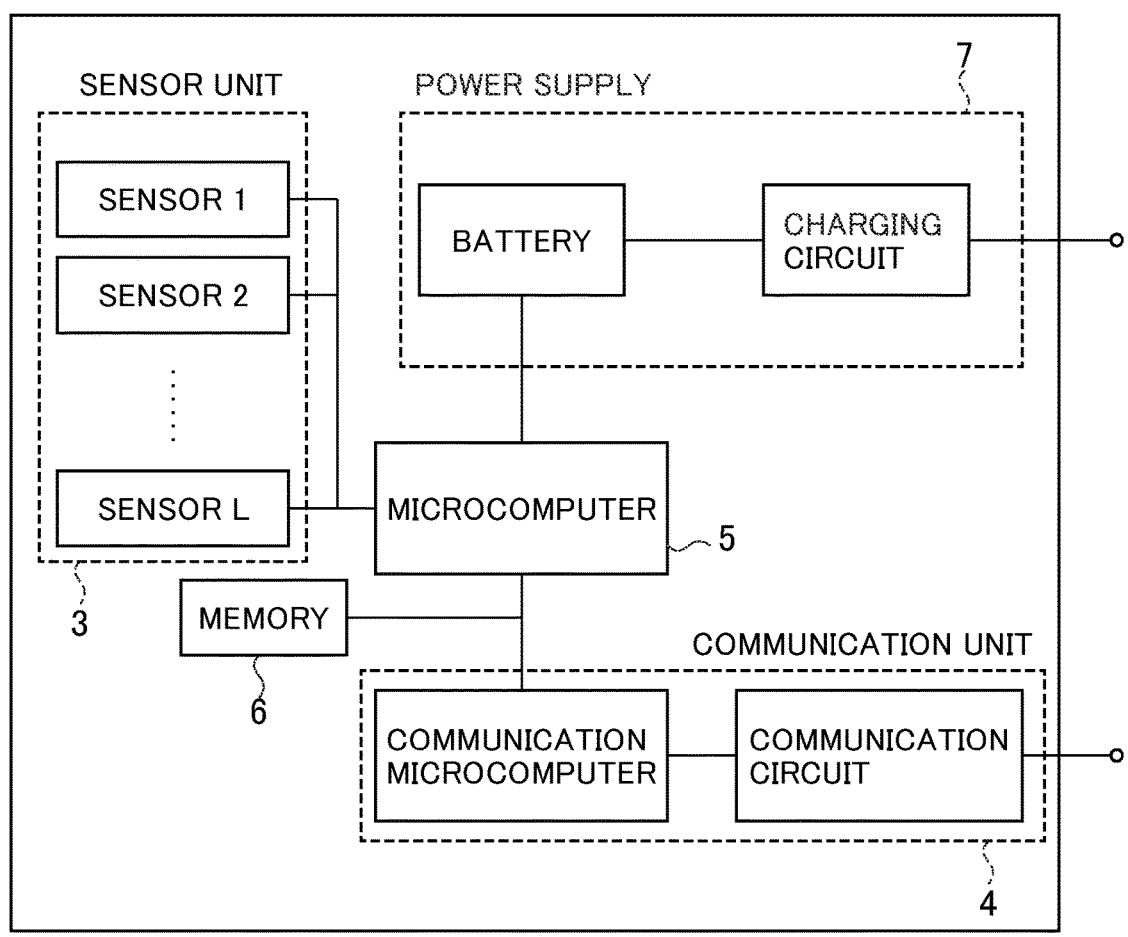
FIG. 7 is a block diagram of a sensor terminal of a second embodiment.

FIG. 7 is a block diagram of a sensor terminal 1. The sensor terminal 1 includes: a sensor unit 3 including a sensor 1 to a sensor L; a communication unit 4 including a communication microcomputer and a communication circuit; a microcomputer 5; a memory 6; and a charging unit 7 including a battery and a charging circuit 7. The sensor 1 to the sensor L that are included in the sensor unit 3 are, for example, acceleration sensors; velocity sensors; GNSS vibration reception devices; temperature sensors; illumination sensors; humidity sensors; or pressure sensors, and the sensor 1 to the sensor L include at least one sensor. It is preferred that the communication unit 4 should perform wireless communication, and should be capable of utilizing, for example, a wireless LAN compliant with IEEE 802.11a, b, g, n, or the like, or a wireless PAN system compliant with Bluetooth (registered trademark), transferjet, UWB or the like. In the case where a wireless communication system is adopted in the communication unit 4, an antenna, a coupler, or the like is connected to the terminal of the communication unit 4. Alternatively, a wire communication system can be adopted to realize the communication unit 4, and in this case, a connector with metal contacts is connected to the connection terminal of the communication unit 4.

The microcomputer 5 performs the control of the sensor 1 to sensor L included in the sensor unit 3, and data output from the sensor 1 to sensor L is stored in the memory 6. In this case, the control of the sensor 1 to sensor L includes turning the power supply of each sensor on and off, switching between operation modes (a measurement mode, a sleep mode, a standby mode, and the like) of each sensor, switching between the ranges of the sensing sensitivity of each sensor, and the like. In FIG. 2, although the microcomputer 5 for controlling the sensor unit 3 and the communication microcomputer are fabricated in separate chips, one microcomputer can be used in common instead of the microcomputer 5 and the communication microcomputer.

A power supply unit 7 supplies electric power accumulated in the battery to each block of the sensor terminal 1. The power supply unit 7 can be charged up via the charging circuit through an external terminal.

Figure 8:
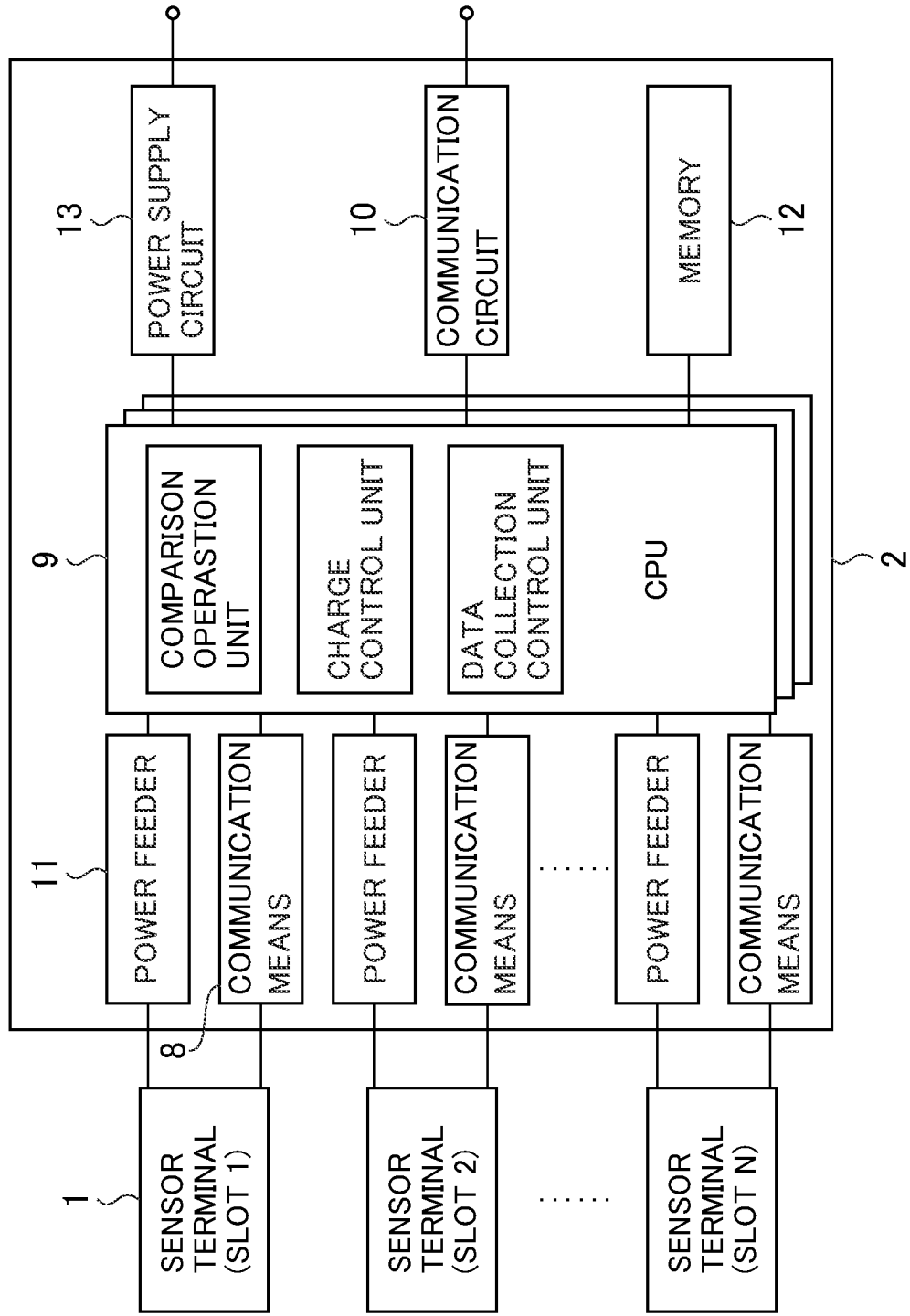
FIG. 8 is a block diagram of the apparatus configuration of the second embodiment.

FIG. 8 is a block diagram of the apparatus configuration. N sensor terminals 1 (wherein N represents the number of sensor terminals 1) are housed in the slot 1 to slot N of a housing device 2 one-on-one (wherein the slot 1 to the slot N are slots each of which houses a sensor terminal 1 and is disposed at arbitrary coordinates). The housing device 2 includes: plural communication circuits 8 for connecting to the sensor terminals 1; a CPU 9; a communication circuit 10 for connecting to upper external devices; plural power feeding circuits 11 for charging up the sensor terminals 1; a memory 12; and a power supply circuit 13. The housing unit 2 detects that a sensor terminal 1 is mounted in each slot with the use of means (not shown in FIG. 3) for detecting whether a sensor terminal 1 is housed or not, establishes connection to the sensor terminal 1 via a communication circuit 8, and receives a vibration reception signal. A comparison operation unit is installed programmatically in the CPU 9, and the CPU 9 executes a comparison procedure on vibration reception signals. The communication circuit 10 can transfer vibration reception signals or the result of the comparison procedure to an upper server, a storage, and the like. The power feeder 11 can charge the sensor terminals 1 housed in the housing device 2, and that charging procedure is executed on the basis of a charging control unit programmed in the CPU 9. Furthermore, a data collection control unit is programmed in the CPU 9, and data stored in the memories 6 of the sensor terminals 1 can be retrieved via the communication unit 4 and the communication means 8. The retrieved data is accumulated in the memory 12, or transferred to the upper server, and the storage via the communication circuit 10. The power supply circuit 13 feeds electric power to each block in the housing device 2.

Figure 18:
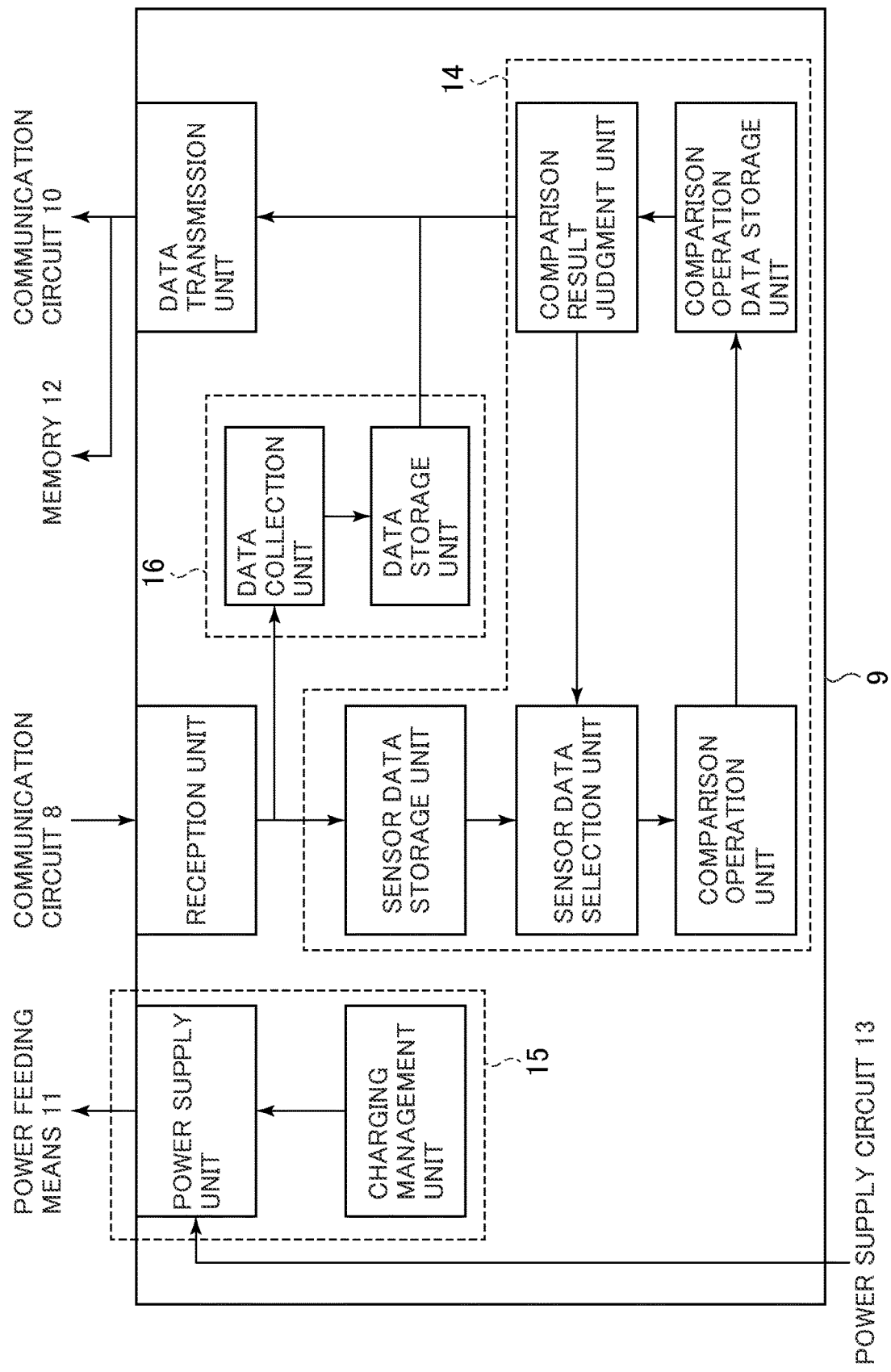
FIG. 18 is a diagram showing an example of a block configuration of internal processing executed by a CPU 9.

FIG. 18 shows an example of a block configuration of internal processing executed by the CPU 9. The CPU 9 includes a block group corresponding to a comparison operation unit 14, a charging control unit 15, and a data collection control unit 16.

First, the comparison operation unit 14 stores sensor data in a sensor data storage unit via a reception unit. Next, at least two data sets are read out by a sensor data selection unit from among the sensor data stored in the sensor data storage unit, the at least two data sets are transferred to the comparison operation unit, and a comparison operation is executed on the at least two data sets. The result of the comparison operation output from the comparison operation unit is stored in a comparison operation data storage unit, and further the agreement or disagreement of the at least two data sets is judged by a comparison result judgment unit with reference to a specific threshold. The judgment result is transmitted to the communication circuit 10 via a data transmission unit, and then the judgment result is stored the upper database or the like. In addition, if the comparison result judgment unit judges that the at least two data sets disagree with each other, the result is reported to the sensor data selection unit, and the data sets that disagree with each other are compared with other data sets to specify an anomalous data set.

In the charging control unit 15, a charging management unit selects a sensor terminal 1 to be charged up from among the sensor terminals 1 mounted in the slots, and issues an order to a power supply unit. The power supply unit supplies electric power from the power supply circuit 13 to a power feeder 11 that is connected to the selected sensor terminal 1.

Figure 9:
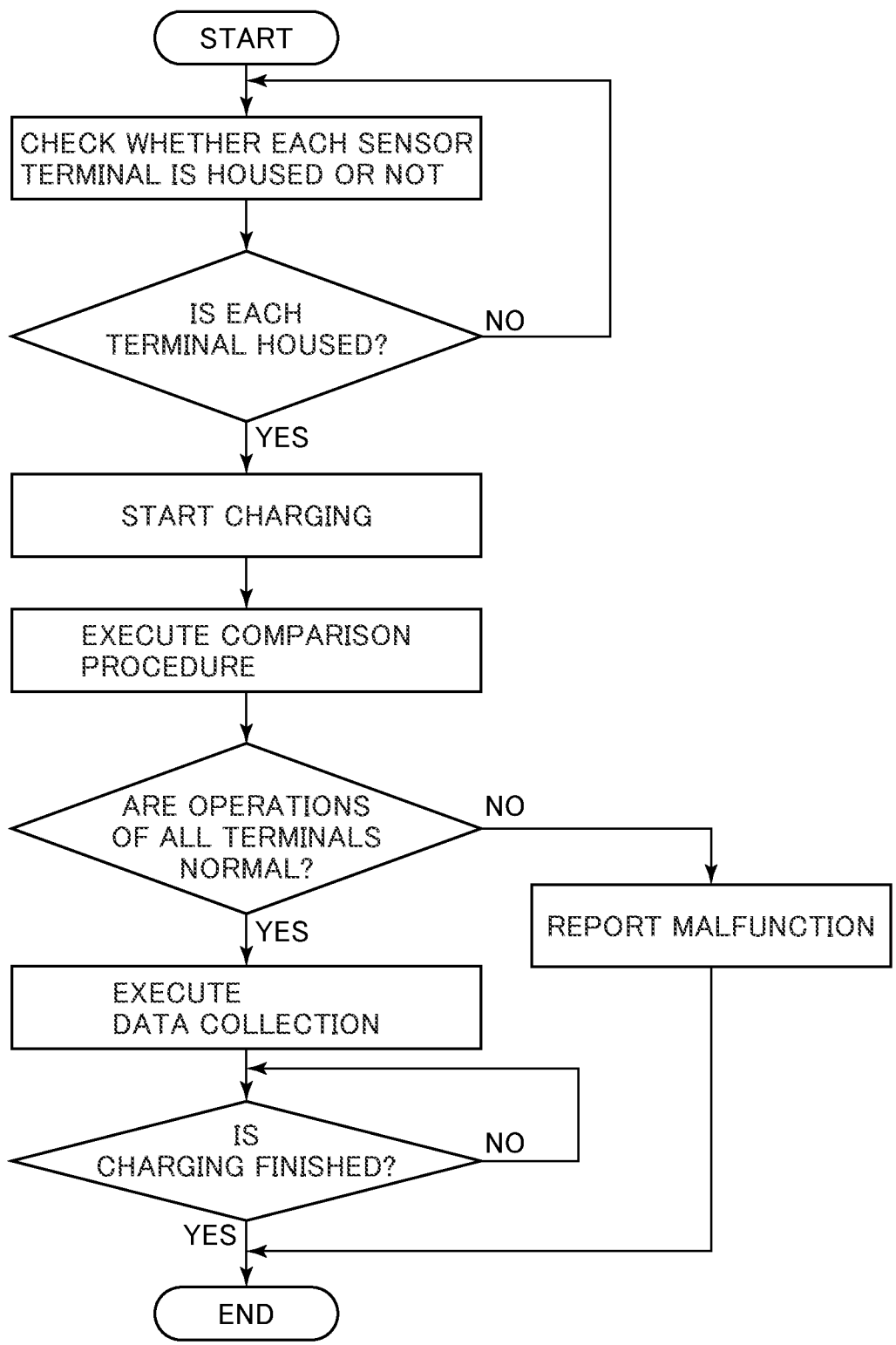
FIG. 9 is a processing flow diagram in the apparatus configuration of the second embodiment.

A data collection unit in the data collection control unit 16 retrieves sensor data accumulated in a sensor terminal 1 via the reception unit. Retrieved sensor data is stored in a data storage unit. The sensor data stored in the data storage unit is stored in the memory 12 via the data transmission unit. Furthermore, some or all of the sensor data is transmitted to the communication circuit 10 via the data transmission unit, and stored in the upper server or the database. FIG. 9 is a processing flow diagram in the apparatus configuration shown in FIG. 8. First, whether each slot is housing a sensor terminal 1 or not is checked by the housing device 2. Next, after it is confirmed that each slot is housing a sensor terminal 1, charging is started. Next, a comparison procedure is executed. In this case, the comparison procedure and the charging are continued in parallel. As a result of the comparison procedure, if it is judged that the operations of all the sensor terminals 1 are normal, data collection is executed. After the data collection is finished, whether the charging is finished or not is checked. When it is confirmed that the charging is finished, the above processing is finished. On the other hand, when, after the data collection is finished, whether the charging is finished or not is checked, and if it is judged that the operation of any terminal 1 is failed or anomalous, the malfunction is reported to the upper server or the like, and the above procedure is finished.

Third Embodiment

In this embodiment, an example of a comparison operation that can be used for a detection method according to the present invention is shown.

Figure 10:
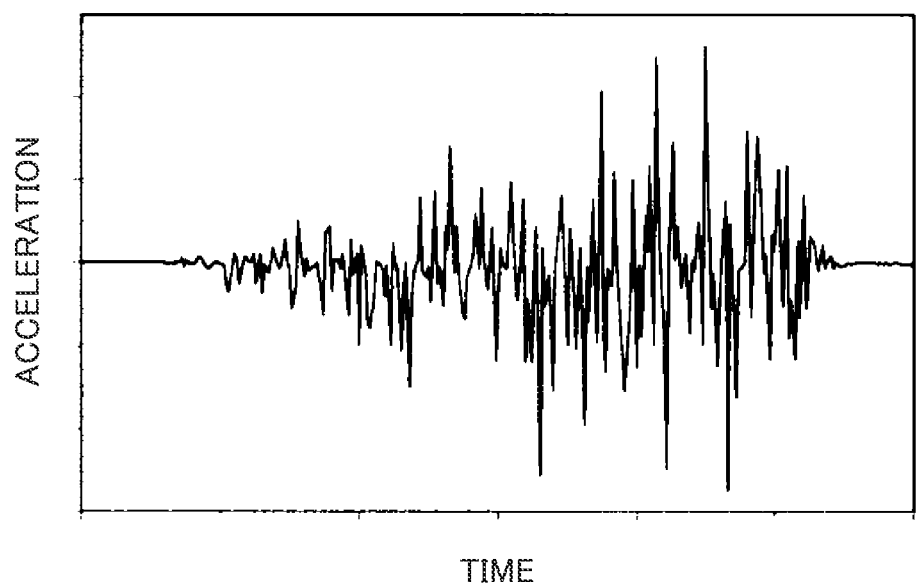
FIG. 10 shows an example of a vibration reception signal output by a sensor terminal.

FIG. 10 shows an example of a vibration reception signal output by a sensor terminal. In this case, the vibration reception signal is time-series acceleration data. Although the sampling time-interval for the time-series acceleration data is within several microseconds and several milliseconds, any other value can be adopted as the sampling time-interval in accordance with the request level of the accuracy of analysis. In seismic exploration, data output by a one-dimensional acceleration sensor, the direction of which is vertical to the ground surface, is generally used. However, in more advanced seismic exploration, it is conceivable that data obtained by a three-axis acceleration sensor and other auxiliary sensors is used.

Figure 11:
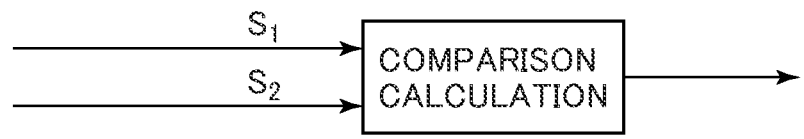
FIG. 11 is a block diagram of a first example of the comparison operation of a third embodiment.

FIG. 11 is a block diagram of a first example of the comparison operation. A comparison calculation is executed on vibration reception signals $s_1$ and $s_2$ output by a first and a second sensor terminals 1 respectively. Here, the comparison calculation is, for example, a calculation that is routinely used in statistical processing such as a mean square error and a cross-correlation function, and it is conceivable that noise canceling is executed as the preprocessing of the vibration reception signals.

Figure 12:
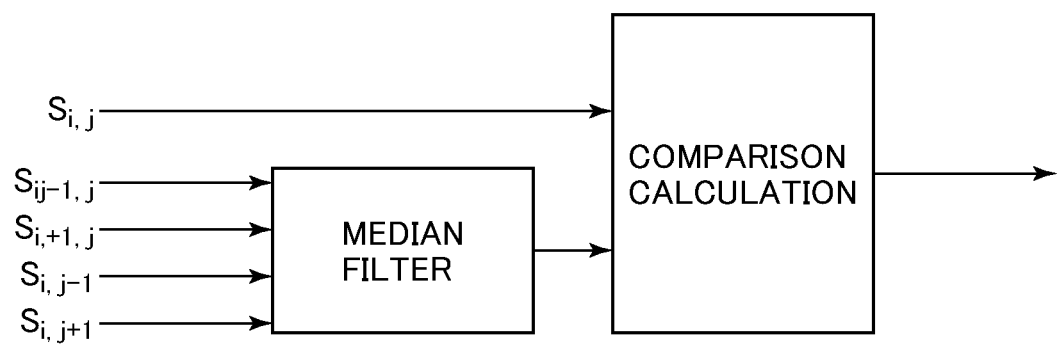
FIG. 12 is a block diagram of a second example of the comparison operation of the third embodiment.

FIG. 12 is a block diagram of a second example of the comparison operation. Vibration reception signals are represented with coordinates of slots explained in FIG. 4 as their suffixes. A vibration reception signal $s_{i,j}$ of a sensor terminal 1 housed in a slot (i, j) is compared with vibration signals $s_{i-1,j}$, $s_{i+1,j}$, $s_{i,j-1}$, $s_{i,j+1}$ of sensor terminals 1 housed in a slot (i−1, j), a slot (i+1, j), a slot (i, j−1), and a slot (i, j+1) respectively. In this case, it is assumed that each of the slot (i−1, j), the slot (i+1, j), the slot (i, j−1), and the slot (i, j+1) houses a sensor terminal 1, but if there is a slot that does not house a sensor terminal, data concerning the slot should be omitted, or data concerning a slot adjacent to the slot (i, j) other than the slot (i−1, j), the slot (i+1, j), the slot (i, j−1), and the slot (i, j+1) can be used instead. Data concerning an adjacent slot is well in synchronization with the data concerning the slot (i, j) in terms of time because the propagation delay of a vibration that is brought about from outside exerts a negligible influence on the data concerning the adjacent slot, hence it is possible to make judgment through a highly accurate comparison. In FIG. 12, a time-series signal (referential vibration reception signal) obtained by calculating the median of the vibration signals $s_{i-1,j}$, $s_{i+1,j}$, $s_{i,j-1}$, and $s_{i,j+1}$ is generated to be used for the comparison. In the above comparison, the average of the vibration signals $s_{i-1,j}$, $s_{i+1,j}$, $s_{i,j-1}$, and $s_{i,j+1}$ can be used instead of the median, or other statistical values based on the vibration signals $s_{i-1,j}$, $s_{i+1,j}$, $s_{i,j-1}$, and $s_{i,j+1}$ can also be used. By comparing the vibration reception signal $s_{i,j}$ with the time-series data that is the median of vibration signals $s_{i-1,j}$, $s_{i+1,j}$, $s_{i,j-1}$, $s_{i,j+1}$, the failure or anomaly of the sensor terminal 1 housed in the slot (i, j) is detected.

At the occasion of the comparison operation, it is conceivable that some combination or another of the above-described plural comparison calculations is executed.

Fourth Embodiment

In this embodiment, an example of a structure of a housing device 2 that can be used for a detection method according to the present invention is shown.

Figure 13:
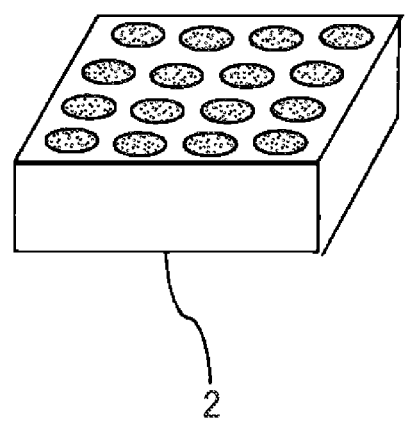
FIG. 13 is a schematic diagram of a first example of a housing device of a fourth embodiment.

FIG. 13 is a schematic diagram of a first example of the housing device 2. Although the housing device 2 shown in FIG. 1 is a rack-type housing device in which sensor terminals 1 are inserted horizontally, a planarly disposed housing device, in which sensor terminals 1 are inserted vertically as shown in FIG. 13, can also be used. The structure of this type of housing device 2 is suitable for housing a comparable small number of sensor terminals 1, and the portability of this type of housing device 2 is excellent.

Figure 14:
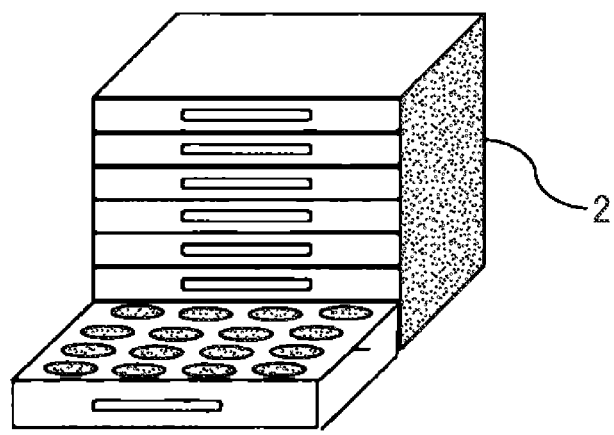
FIG. 14 is a schematic diagram of a second example of a housing device of the fourth embodiment.

FIG. 14 is a schematic diagram of a second example of the housing device 2. FIG. 14 shows a drawer type housing device including plural planarly disposed housing devices 2 piled vertically. This type of housing device 2 can house a large number of sensor terminals 1.

Figure 15:
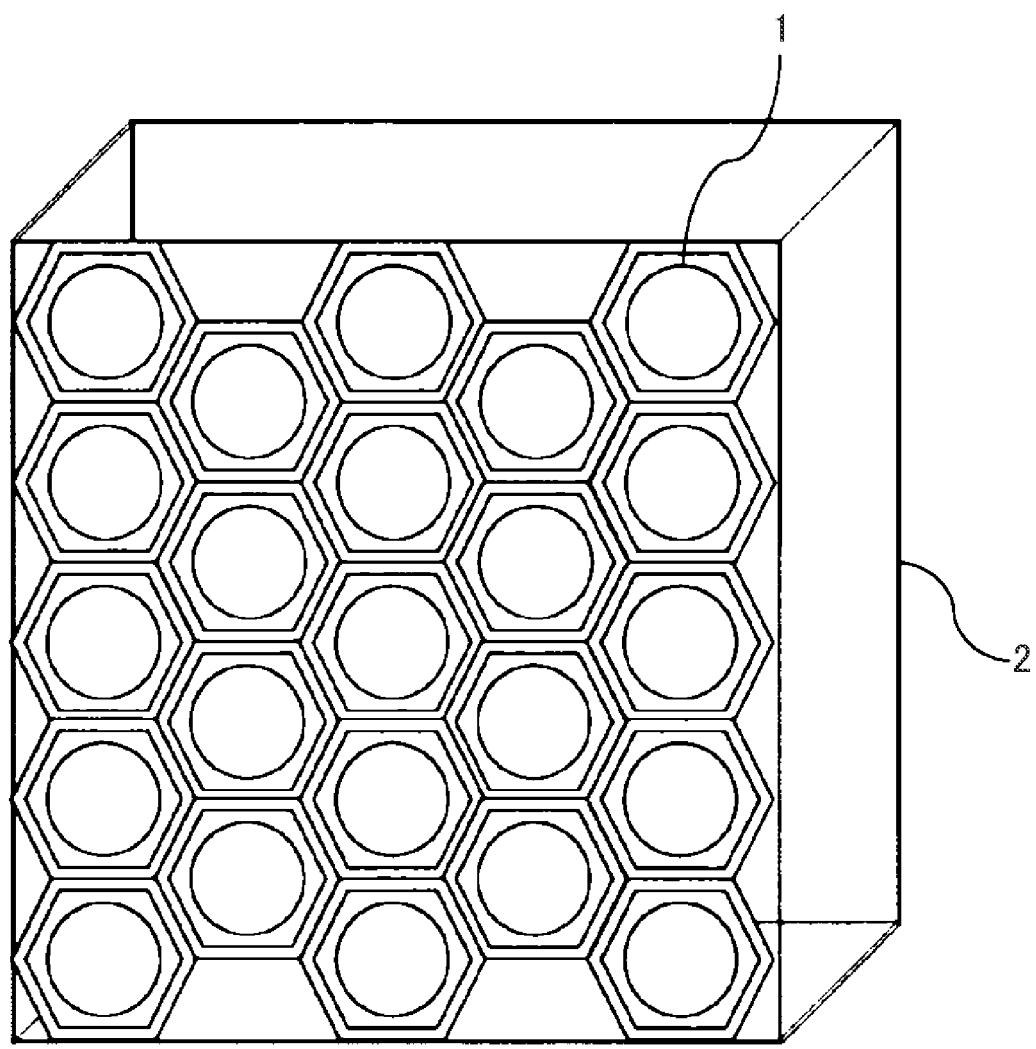
FIG. 15 is a schematic diagram of a third example of a housing device of the fourth embodiment.

FIG. 15 is a schematic diagram of a third example of the housing device 2. Although all the housing devices 2 shown in FIG. 1, FIG. 13, and FIG. 14 have configurations in which sensor terminals 1 are arranged in the shape of a grid lattice, it is not always necessary that sensor terminals 1 should be arranged in the shape of a grid lattice, and, for example, FIG. 15 shows sensor terminals 1 are arranged in the shape of a hexagonal lattice. There may be some cases where the efficiency of housing sensor terminals 1 becomes higher by arranging the sensor terminals in the shape of a hexagonal lattice depending on the shapes of the sensor terminals 1.

As for the rest, from the view point of the housing efficiency and usability of the housing device 2, various configurations of the housing device 2 and various arrangement methods of sensor terminals 1 may be available.

LIST OF REFERENCE SIGNS

1: Sensor Terminal
2: Housing Device
3: Sensor Unit
4: Communication Unit
5: Microcomputer
6: Memory
7: Power Supply Unit
8: Communication Means
9: CPU
10: Power Supply Circuit
11: Power Feeder
12: Memory
13: Power Supply Circuit
14: Comparison Operation Unit
15: Charging Control Unit
16: Data Collection Unit

The invention claimed is:
1. A method of detecting the failure or anomaly of a sensor terminal, comprising:

preparing a plurality of sensor terminals having sensors that detect vibrations from outside, the plurality of sensor terminals receiving the vibrations and outputting vibration reception signals; and comparing a first vibration reception signal output from a first sensor terminal with a second vibration reception signal output from a second sensor terminal, thereby detecting that at least one of the first and second terminals has failed or is anomalous, wherein slots of a housing unit for housing the plurality of sensor terminals are arranged in a shape of a lattice, and the first sensor terminal and the second sensor terminal are selected from among sensor terminals housed in slots located adjacently.

2. The method of detecting the failure or anomaly of a sensor terminal according to claim 1, wherein the first sensor terminal and the second sensor terminal are installed adjacently.

3. The method of detecting the failure or anomaly of a sensor terminal according to claim 1, wherein the vibrations from outside are natural vibrations propagated from the outside of the sensors.

4. A method of detecting failure or anomaly of a sensor terminal, comprising:

preparing a plurality of sensor terminals having sensors that detect vibrations from outside, the plurality of sensor terminals receiving the vibrations and outputting vibration reception signals;

comparing a first vibration reception signal output from a first sensor terminal having a first sensor with a reference vibration reception signal calculated on basis of vibration reception signals output from at least two other sensor terminals; and detecting the failure or anomaly of the first sensor, wherein the plurality of sensor terminals are housed in slots arranged in a shape of a lattice on one-on-one basis, and the first sensor terminal and the at least two other sensor terminals are selected from among sensor terminals housed in slots located adjacently.

5. The method of detecting the failure or anomaly of a sensor terminal according to claim 4, wherein the vibrations from outside are natural vibrations propagated from outside of the sensors.

* * * * *